United States Patent
Fatiny (10) Patent No.: US 10,321,977 B1
(45) Date of Patent: Jun. 18, 2019

(54) DENTAL DEVICE

(71) Applicant: King Abdulaziz University, Jeddah (SA)

(72) Inventor: Fahad Ibrahim Fatiny, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/832,284

(22) Filed: Dec. 5, 2017

(51) Int. Cl.
- *A61C 1/16* (2006.01)
- *A61C 5/90* (2017.01)
- *A61C 1/08* (2006.01)

(52) U.S. Cl.
CPC ............. *A61C 5/90* (2017.02); *A61C 1/16* (2013.01); *A61C 1/081* (2013.01); *A61C 1/082* (2013.01)

(58) Field of Classification Search
CPC .. A61C 5/90; A61C 1/16; A61C 1/082–1/085; A61C 1/081; A61C 5/44; A61B 17/176; A61B 2090/033; A61B 2090/034; A61B 2090/036; B23B 49/003; B23B 49/005; B23B 49/006; B23B 49/008
USPC ............................................ 606/172; 30/286
See application file for complete search history.

(56) References Cited

U.S. PATENT DOCUMENTS

| | | | |
|---|---|---|---|
| 1,067,571 A | 7/1913 | Abbott | |
| 1,152,122 A * | 8/1915 | Samphere | A61C 1/16 15/23 |
| 1,285,273 A * | 11/1918 | Luzzi | A61C 1/16 433/116 |
| 2,671,269 A | 3/1954 | Francis et al. | |
| 2,731,722 A | 1/1956 | Wilen | |
| 2004/0038182 A1* | 2/2004 | Zappini | A61C 13/267 433/178 |
| 2007/0042325 A1* | 2/2007 | Florman | A61C 1/16 433/116 |
| 2008/0014550 A1* | 1/2008 | Jones | A61C 1/0015 433/114 |
| 2010/0173259 A1* | 7/2010 | Vogel | A61C 1/084 433/72 |

FOREIGN PATENT DOCUMENTS

| | | |
|---|---|---|
| CA | 2182726 A1 | 9/1997 |
| CH | 602086 | 7/1978 |
| CN | 201564621 U | 9/2010 |
| FR | 2228463 A1 | 12/1974 |

* cited by examiner

*Primary Examiner* — Edward Moran
(74) *Attorney, Agent, or Firm* — Oblon, McClelland, Maier & Neustadt, L.L.P.

(57) ABSTRACT

A dental device includes a rounded flexible device configured to attach onto a head of a dental drill. The rounded flexible device has a first pair of opposing horizontal protrusions positioned at a first end of the rounded flexible device; a second pair of opposing horizontal protrusions positioned at a mid-portion of the rounded flexible device, wherein the first pair of opposing horizontal protrusions extend horizontally beyond the second pair of opposing horizontal protrusions; and a central vertical protrusion positioned at a second end of the rounded flexible device. The first pair and the second pair of opposing horizontal protrusions are configured to partially encircle the head of the dental drill, and the central vertical protrusion is configured to extend a length of a rotating drill bit of the dental drill.

12 Claims, 9 Drawing Sheets

DENTAL DEVICE

BACKGROUND

Field of the Invention

Embodiments described herein include a dental device. In particular, embodiments include a dental guard configured to protect a dental patient's mouth during dental treatment.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

A dental drill is a small, high-speed drill used during dental procedures, such as removing decay and shaping a tooth structure prior to insertion of a filling or a crown. The fast speed of the dental drill produces instinctive body and tongue movements when the patient suddenly feels pain. These body and tongue movements tend to be pronounced with children. The drill bit, also known as a bur, does not stop immediately due to inertia of the rotating bur. This can cause damage to the oral mucosa and tongue of the patient.

SUMMARY

In an exemplary embodiment, a dental device includes a rounded flexible device configured to attach onto a head of a dental drill. The rounded flexible device has a first pair of opposing horizontal protrusions positioned at a first end of the rounded flexible device; a 25 second pair of opposing horizontal protrusions positioned at a mid-portion of the rounded flexible device, wherein the first pair of opposing horizontal protrusions extend horizontally beyond the second pair of opposing horizontal protrusions; and a central vertical protrusion positioned at a second end of the rounded flexible device. The first pair and the second pair of opposing horizontal protrusions are configured to partially encircle the head of the dental drill, and the central vertical protrusion is configured to extend a length of a rotating drill bit of the dental drill.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The following descriptions are meant to further clarify the present disclosure by giving specific examples and embodiments of the disclosure. These embodiments are meant to be illustrative rather than exhaustive. The full scope of the disclosure is not limited to any particular embodiment disclosed in this specification, but rather is defined by the claims.

It will be appreciated that in the development of any such actual implementation, numerous implementation-specific decisions need to be made in order to achieve the developer's specific goals, such as compliance with application- and business-related constraints, and that these specific goals will vary from one implementation to another and from one developer to another.

A dental drill bit can cause damage to the oral mucosa of a patient, which causes pain and may infringe upon completion of the dental procedure. An exemplary conventional protective device has an outer sleeve with locking wings arranged on an inner wall of the outer sleeve. It also includes a drill protective shield. The exemplary conventional protective device mounts onto a bend in the grip or handle of a turbine in the drill. It includes a fixing hook with a protective wall. The wall pivots relative to the fixing hook about a geometrical axis, which is parallel to the axis of the drill when in use.

When a tooth is drilled, it may be necessary to work on both sides of the tooth, i.e. on the cheek side and on the tongue side. It may also be necessary to work on the sides close to adjacent teeth. In such a case, the drill can butt against the adjacent teeth. An exemplary conventional protective device may need to be removed before working between two teeth with the drill. Also, an exemplary conventional protective device may be limited to working only on a middle area of the tongue side since the width of the protective wall causes it to encounter adjacent teeth well before the drill arrives in the proximity of the adjacent tooth.

An objective of embodiments described herein is to provide a protective dental device that protects the soft tissues of a patient's mouth, but also enables a dental practitioner to drill from any point on the side of a tooth. The protective dental device allows drilling the tooth from a close proximity of a first adjacent tooth to a close proximity of a second adjacent tooth that is located at the opposite end of the tooth being drilled.

Another objective is to provide a protective dental device that prevents serious lacerations of the tongue and mouth of a patient which can occur during a drilling operation through involuntary movements of the patient, or through the inability of the dental practitioner to control the patient's tongue and cheek with his/her fingers or with conventional instruments. High-speed dental drills are capable of causing severe damage to the mouth tissue in a very short period of time.

Another objective is to provide a protective dental device which mounts on a drill head. It includes an elongated deflector surface, which is suitably spaced from the drill to prevent a patient's tongue from contacting the drill bit or becoming entangled with it. The protective dental device is also designed to prevent irritation of delicate mouth tissue or nerve endings and therefore, not activate the glands or muscles in the patient's mouth. The protective dental device also does not cause any discomfort to the patient.

Another objective is to provide a protective dental device that is securely supported solely by the drill. This design provides a free hand to the dental practitioner while drilling. The protective dental device is readily mounted onto and removed from the drill without the use of tools, and has the capacity to be cleaned and sterilized.

Another objective is to provide a protective dental device that is rigid enough to withstand bending and strong forces exerted by a patient. It is also simple in construction, economical to manufacture, and durable in use.

Figure 1:
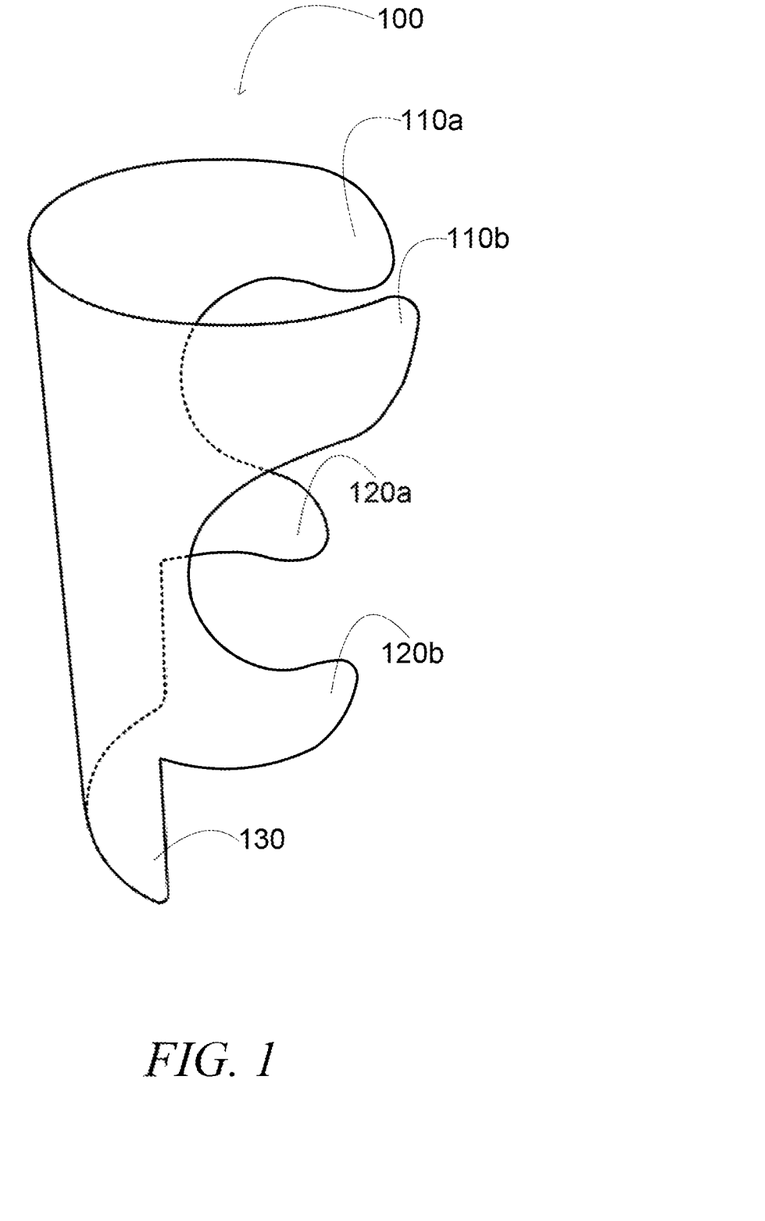
FIG. 1 is a schematic illustrating a protective dental device according to one embodiment.

FIG. 1 is a schematic illustrating a protective dental device 100 configured to achieve the objectives described herein. A first pair of opposing flanges 110a and 110b is positioned on an upper end of the protective dental device 100. A second pair of opposing flanges 120a and 120b is positioned on a mid portion of the protective dental device 100. The first pair of opposing flanges 110a and 110b is longer and extends farther outward than the second pair of opposing flanges 120a and 120b. In one embodiment, the first pair of opposing flanges 110a and 110b extends approximately 50% farther than the second pair of opposing flanges 120a and 120b from a central spine region of the protective dental device 100. A lower protrusion 130 extends vertically below the second pair of opposing flanges 120a and 120b. In an embodiment, the lower protrusion 130 is transparent to provide visibility of a drill bit. The first pair of opposing flanges 110a and 110 b is preferably at least 20% longer than the second pair of opposing flanges 120a and 120b, more preferably 30%, 40%, 60%, or 100% longer based on the length measured from the apex of the protrusion to the bottom of the trough formed between the first and second opposing flanges.

Figure 2:
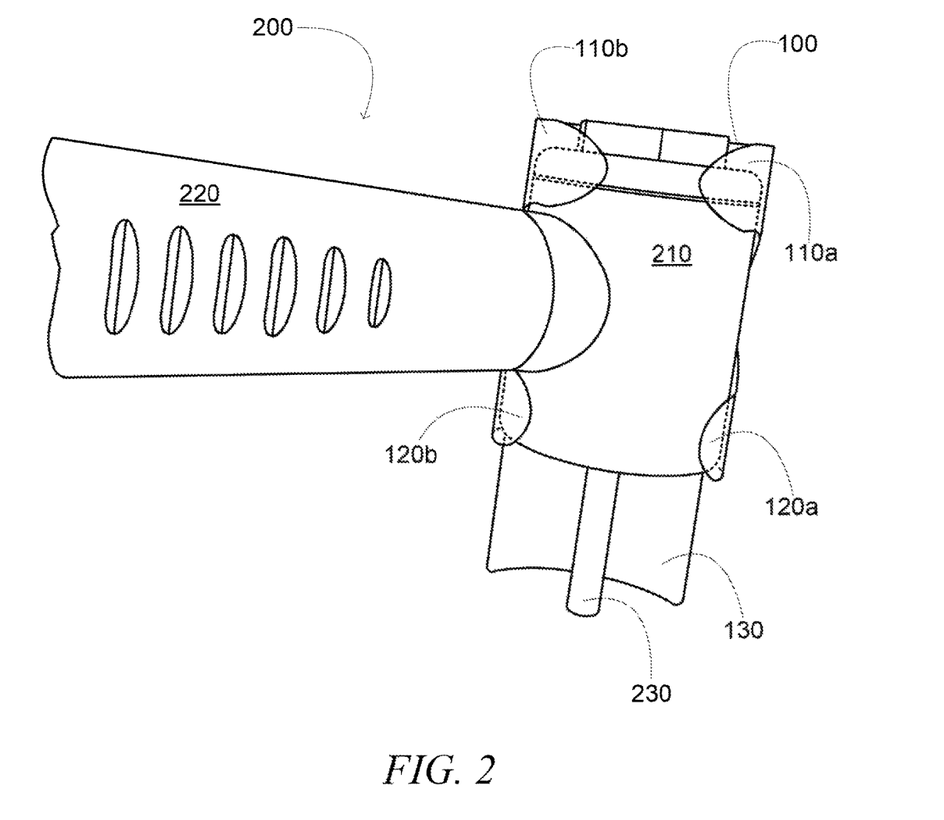
FIG. 2 is a schematic illustrating the protective dental device attached to a dental drill according to one embodiment.

FIG. 2 is a schematic illustrating the protective dental device 100 attached to a dental drill 200. The protective dental device 100 fits around a drill head 210 which extends from a drill handle 220 of the dental drill 200. The first pair of opposing flanges 110a and 110b fits around the drill head 210 on an upper side of the drill handle 220. The second pair of opposing flanges 120a and 120b fits around the drill head 210 on a lower side of the drill handle 220. The lower protrusion 130 extends vertically downward from the second pair of opposing flanges 120a and 120b along a side of a drill bit 230.

As illustrated in FIG. 2, the lower protrusion 130 extends approximately the same length as the drill bit 230 and partially encircles the drill bit 230. The lower protrusion 130 protects other regions of the teeth, gums, and cheek while the drill bit 230 is actively drilling a particular tooth. The lower protrusion 130 can be the same length as the drill bit 230 or slightly shorter or slightly longer than the drill bit 230. Preferably, as illustrated in the Figures, a length of protrusion 130 is defined from a second or bottom end of the device to the bottom flanges 120a and 120b, and the length of protrusion 130 is less than a length of the device measured from the bottom flanges 120a and 120b to a first or top end of the device. FIG. 2 illustrates the lower protrusion 130 encircles the drill bit 230 by approximately 50%. However, the lower protrusion 130 can encircle the drill bit 230 by less than 50% or more than 50%. In some embodiments, the lower protrusion 130 entirely encompasses the circumference area around the drill bit 230. In other embodiments, the lower protrusion 130 is only 80%, 70%, 50%, 40%, or 30% of the circumference of the drill bit 230. The lower edge of the lower protrusion 130 can be a square edge, as illustrated in FIG. 2. In other examples, the lower protrusion 130 can form a tapered lower edge of varying degrees. In particular, the lower edge of the lower protrusion 130 can vary from 90 degrees (i.e. a square lower edge) to 45 degrees (i.e. a pointed lower edge). Specific dimensions and geometries can vary according to specific dental procedures performed and personal preferences of the dental practitioner.

Figures 3A, 3B, 3C:
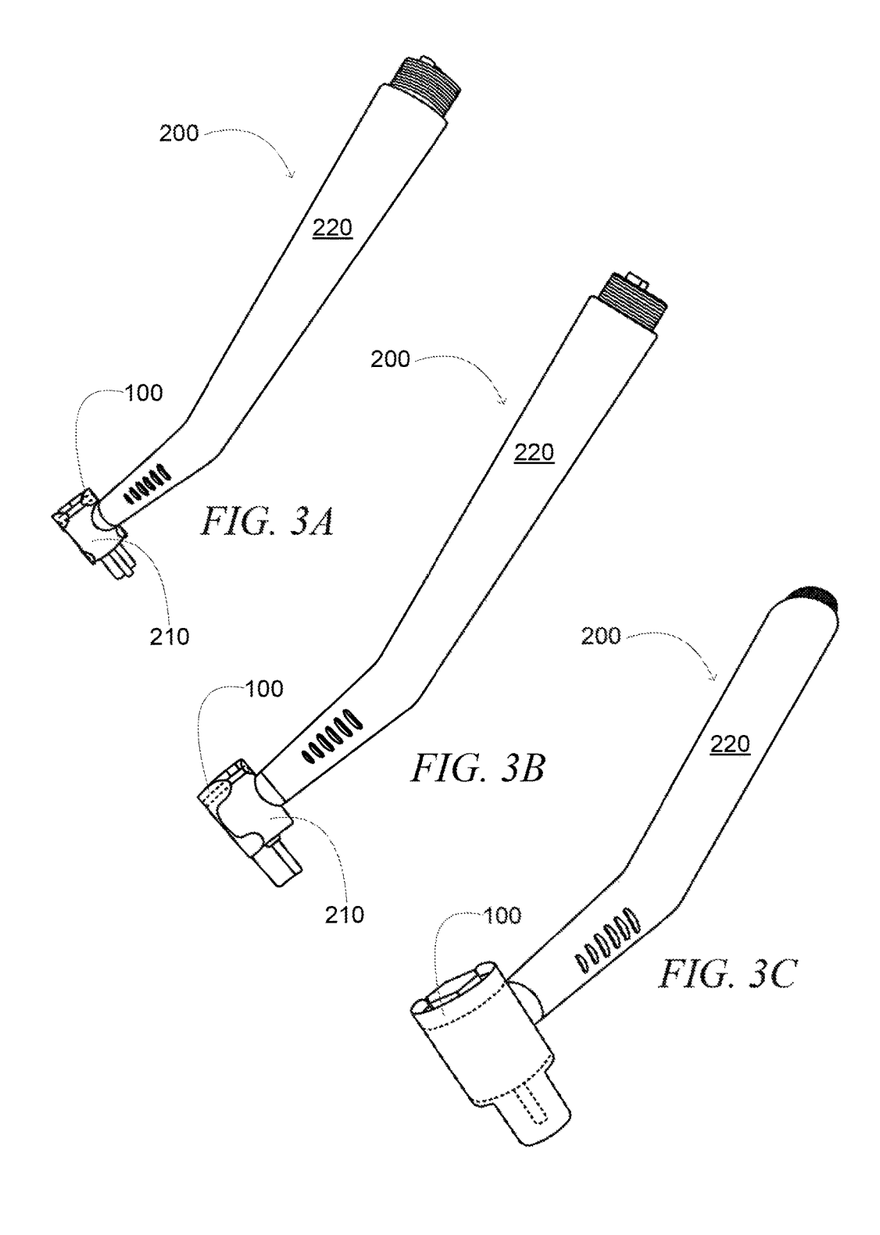
FIG. 3A is a schematic illustrating a protective dental device positioned along a back side of a drill head according to one embodiment.
FIG. 3B is a schematic illustrating a protective dental device positioned in an outer side of a drill head according to one embodiment.
FIG. 3C is a schematic illustrating a protective dental device positioned on a front side of a drill head according to one embodiment.

The protective dental device 100 can easily be rotated relative to the drill head 210 with an opposite hand while holding the drill 200 without the use of external tools. FIG. 3A is a schematic illustrating the protective dental device 100 positioned along a back side of the drill head 210 relative to the drill handle 220. FIG. 3B is a schematic illustrating the protective dental device 100 positioned in an outer side of the drill head 210 relative to the drill handle 220. FIG. 3C is a schematic illustrating the protective dental device 100 positioned on a front side of the drill head 210 (the drill head 210 is out of view in FIG. 3C) relative to the drill handle 220.

In some embodiments, the protective dental device 100 is rotatable about the drill head 210 through fixed positions. A protrusion or concave portion located inside the curvature of the protective dental device 100 can match with one or more protrusions or concavities on the outer surface of the drill head 210. For example, a protrusion on the inner surface of the protective dental device 100 may mate with a concave portion of the drill head 210 such that the dental protective device 100 is affixed in a particular position. Other protrusions or concavities on the surface of the drill head 210 may permit additional fixed positions at which the protective dental device 100 may be at least temporarily affixed with a resistance to turning or readjustment of position. Rotational readjustment of the dental protective device 100 about the axis of the drill head 210 may be facilitated by the inclusion of one or more appendages or protrusions that extend substantially from the surface of either the lower protrusion 130 or the opposing flanges 110a, 110b or 120a, 120b. Such protrusions permit an operator of the protective dental device 100 to quickly adjust the positioning of the protective dental device 100 with one hand, such as by rotating the protective dental device 100 about the axis of the drill head 210 by pushing on the protrusion with a thumb or finger of the hand that is holding the protective dental device 100.

Figure 4:
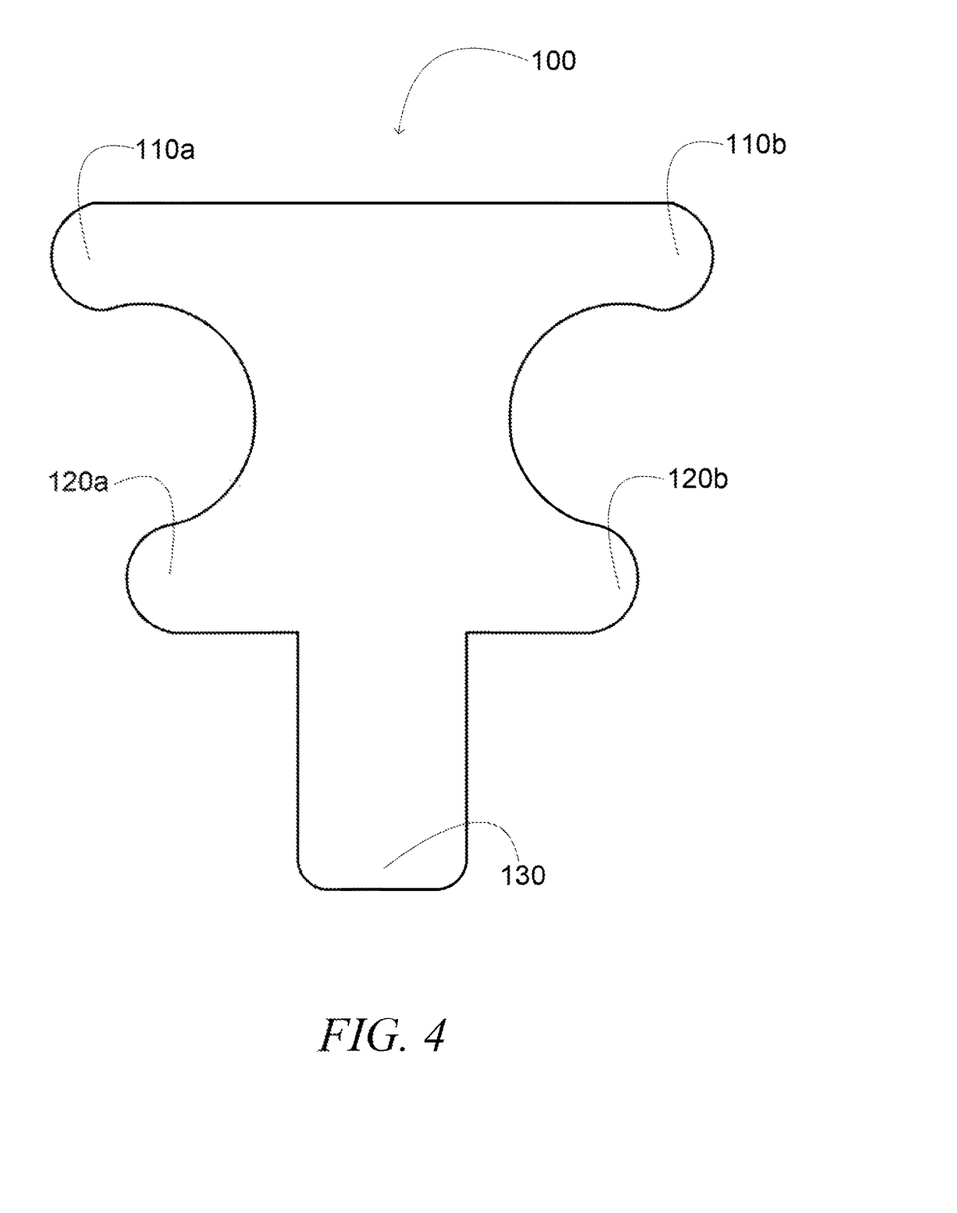
FIG. 4 is a schematic illustrating a protective dental device in a flat orientation according to one embodiment.

FIG. 4 is a schematic illustrating the protective dental device 100 in a flat orientation, such as during initial manufacturing. In one embodiment, multiple protective dental devices 100 can be cut into their initial flat geometry, such as the geometry illustrated in FIG. 4 from a continuous flat sheet of material. In a second embodiment, the protective dental device 100 can be molded into its final shape, such as the geometry illustrated in FIG. 1 via a mold injection process.

Materials for the protective dental device 100 can range from multiple types of plastic or polymer materials, metal or metal alloy materials, or several hybrid or composite materials. A list of biocompatible polymer materials which can be used for the protective dental device 100 includes, but is not limited to polylactic acid (PLA), poly(lactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), silicone, polyurethane, thermoplastic elastomer (TPE) such as a styrenic block copolymer (TPE-s), a thermoplastic olefin (TPE-o), an elastomeric alloy (TPE-v or TPV), a thermoplastic polyurethane (TPU), a thermoplastic copolyester (TPE-E), or a thermoplastic polyamide.

Several processes can be used to obtain the 3-dimensional structure of the protective dental device 100. In one example, a shape-memory polymer (SMP) can be used to form and maintain the 3-dimensional structure of the protective dental device 100. An SMP has the ability to return from a deformed temporary shape to its original permanent shape, which is induced by an external stimulus such as a temperature change, an electric field, a magnetic field, light, or a chemical solution. SMPs include thermoplastic and thermoset polymeric materials.

When a polymer has been manufactured by conventional methods to form its permanent state, the material can be changed into another temporary state or shape by a process of heating, deformation, and cooling. The polymer maintains the temporary shape until the permanent shape is activated by a predetermined external stimulus.

SMPs have at least two separate phases. The phase showing the highest thermal transition, $T_{perm}$ is the temperature that must be exceeded to establish the physical cross-links responsible for the permanent shape. Switching segments of the material have the ability to soften past a certain transition temperature, $T_{trans}$ and are responsible for the temporary shape. In some cases, the transition temperature can be the glass transition temperature, $T_g$ or the melting temperature, $T_m$ of the material. Exceeding the $T_{trans}$ (while still remaining below the $T_{perm}$) activates the switching by softening the switching segments and thereby allowing the material to resume its original permanent form.

SMPs can be used with embodiments described herein for the protective dental device 100. An SMP material, including but not limited to PU, PET, and block copolymers such as PS and poly(1,4-butadiene) can be cut to the desired geometry, such as the shape illustrated in FIG. 4. The cut SMP material can be heated to its respective $T_{perm}$, shaped to its desired 3-dimensional structure such as the shape illustrated in FIG. 1, then cooled. A flexible 3-dimensional structure such as the protective dental device 100 illustrated in FIG. 1 is achieved. Preferably, the protective dental device 100 is made of a thermoplastic material. The protective dental device 100 can be made by injection molding the entire shape such that it is pre-formed with a curvature that fits the drill head 210. Materials of different stiffness or transparency can be used depending on the particular application and whether an oral hygienist or dentist needs a particular perspective of the operating area. Alternately, the protective dental device 100 may be injection molded or cast to form a device having an adhesive on one side. The adhesive serves to hold the protective dental device 100 onto the drill head 210 as the protective dental device 100 is wrapped there around. Preferably, the protective dental device 100 is formed by injection molding a thermoplastic material into a mold which imparts a tangible three-dimensional curved shape to the protective dental device 100. In this embodiment, the protective dental device 100 maintains its curvature both during storage and during use. Depending on the stiffness and thickness of the protective dental device 100, it may be "snapped onto" the drill head 210 in a manner that provides security and hold thereto.

Figure 5:
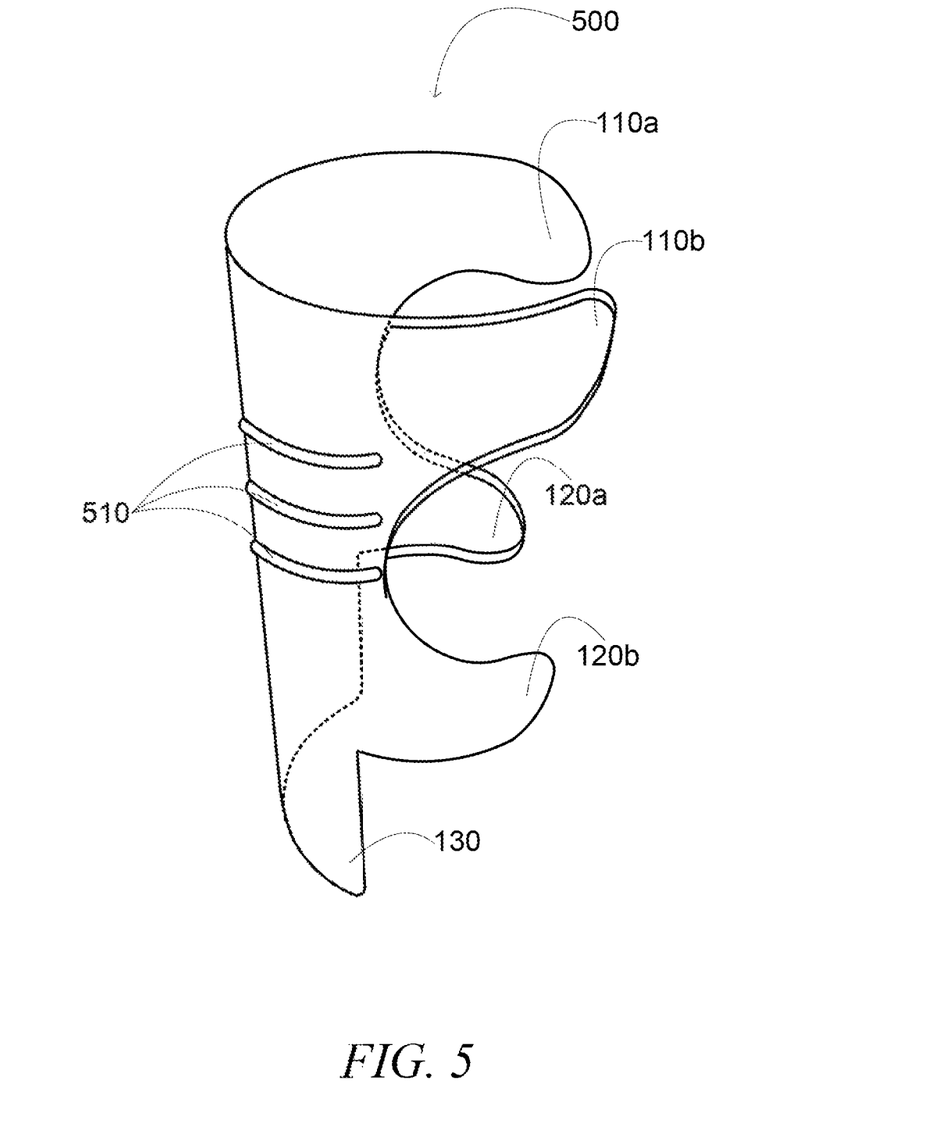
FIG. 5 is a schematic illustrating a protective dental device according to one embodiment.

FIG. 5 is a schematic illustrating protective dental device 500. The protective dental device 500 has a similar 3-dimensional structure as protective dental device 100, except protective dental device 500 has horizontal protrusions 510 along the exterior surface. FIG. 5 illustrates three horizontal protrusions 510. However, less than three or more than three horizontal protrusions 510 are contemplated by embodiments described herein.

The protrusions 510 are preferably made of a material having a different coefficient of thermal expansion or a different elasticity in comparison to the material used to form the dental protective device 500. In this manner, the protrusions 510 act as springs which function to impart curvature to the dental protective device 500. In one embodiment, the curvature comprises a metal spring which imparts a near-permanent curvature to the dental protective device 500.

Figure 6:
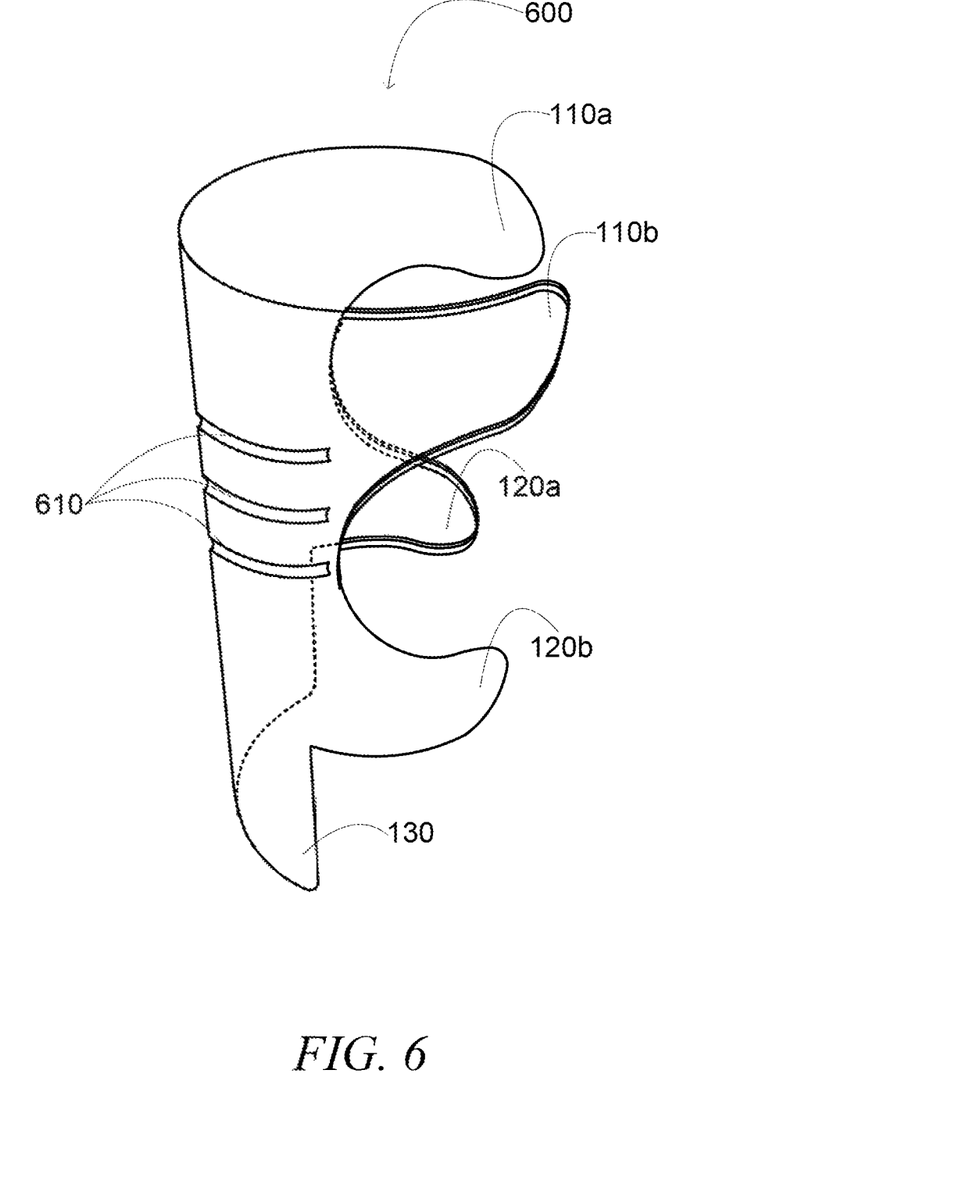
FIG. 6 is a schematic illustrating a protective dental device according to one embodiment.

FIG. 6 is a schematic illustrating protective dental device 600. The protective dental device 600 has a similar 3-dimensional structure as protective dental device 100, except protective dental device 600 has horizontal depressions 610 along the exterior surface. FIG. 6 illustrates three horizontal depressions 610. However, less than three or more than three horizontal depressions 610 are contemplated by embodiments described herein. In embodiments in which depressions are formed on the inside surface of the dental protective device 600, these function in a manner to impart spring-like reflexivity and holding capacity to the dental protective device 600 as it is mounted on the drill head 210.

Figure 7A:
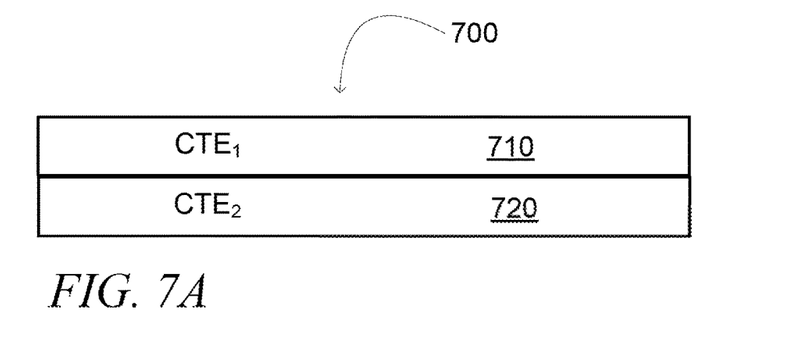
FIG. 7A is a schematic illustrating a cross-sectional view of a flat manufactured material to be used for a protective dental device according to one embodiment.

FIG. 7A is a schematic illustrating a cross-sectional view of a flat manufactured material to be used for a protective dental device 700. FIG. 7A illustrates a laminated material. A first layer 710 includes a material having a first coefficient of thermal expansion ($CTE_1$). A second layer 720 includes a material having a second coefficient of thermal expansion ($CTE_2$). In one embodiment, $CTE_1$ is not equal to $CTE_2$.

Figure 7B:
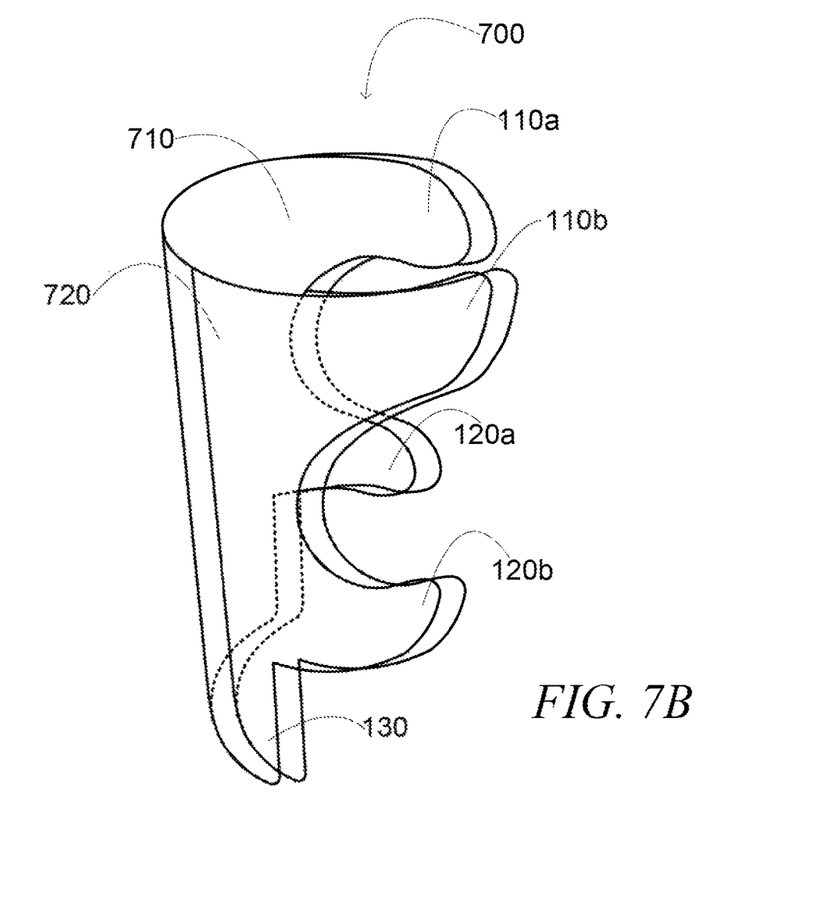
FIG. 7B is a schematic illustrating a cross-sectional view of a protective dental device in a final 3-dimensional structure according to one embodiment.

FIG. 7B is a schematic illustrating a cross-sectional view of protective dental device 700 in a final 3-dimensional structure. The first layer 710 is positioned on an inner surface of the final 3-dimensional structure of the protective dental device 700. The second layer 720 is positioned on an outer surface of the final 3-dimensional structure of the protective dental device 700.

FIG. 7B illustrates how it can be advantageous for $CTE_2$ of the second layer 720 to be greater than $CTE_1$ of the first layer 710. The exterior surface area (outer circumference) of the second layer 720 is greater than the exterior surface area (inner circumference) of the first layer 710. For a predetermined change in temperature, the degree of expansion of the second layer 720 will be greater than the degree of expansion of the first layer 710 due to the higher $CTE_2$ of the second layer 720. As a result, the greater degree of expansion of the second layer 720 will cause less stress between the first layer 710 and the second layer 720 in response to a temperature change. In contrast, more stress will likely be caused if $CTE_E$ of the first layer 710 is equal to $CTE_2$ of the second layer 720 or if the protective dental device 700 comprises a single homogenous material. Likewise, even more stress will likely be caused if $CTE_1$ of the first layer 710 is greater than $CTE_2$ of the second layer 720.

Figure 8A:
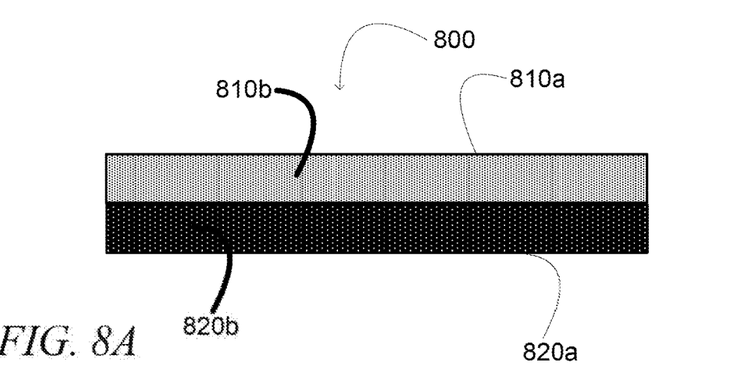
FIG. 8A is a schematic illustrating a cross-sectional view of a flat manufactured material to be used for a protective dental device according to one embodiment.

FIG. 8A is a schematic illustrating a cross-sectional view of a flat manufactured material to be used for a protective dental device 800. FIG. 8A illustrates a laminated material. A first layer 810a includes a material having a first filler 810b. A second layer 820a includes a material having a second filler 820b. In one embodiment, the first filler 810b is different from the second filler 820b. For example, the first filler 810b and the second filler 820b could have different CTEs. In another example, the size of particles of the first filler 810b could differ from the size of particles of the second filler 820b.

Figure 8B:
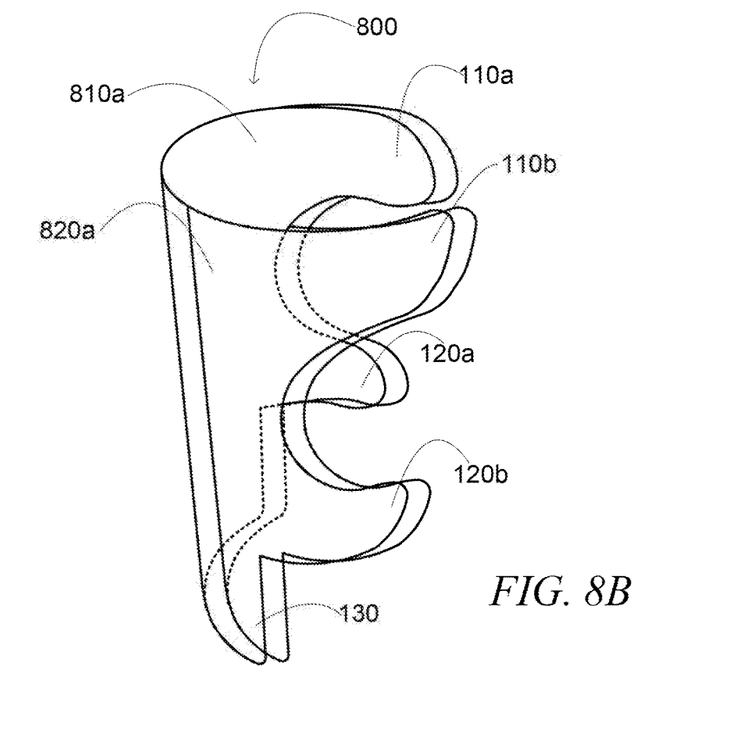
FIG. 8B is a schematic illustrating a cross-sectional view of a protective dental device in a final 3-dimensional structure according to one embodiment.

FIG. 8B is a schematic illustrating a cross-sectional view of protective dental device 800 in a final 3-dimensional structure. The first layer 810a is positioned on an inner surface of the final 3-dimensional structure of the protective dental device 800. The second layer 820a is positioned on an outer surface of the final 3-dimensional structure of the protective dental device 800. If the CTE of the first filler 810b is less than the CTE of the second filler 820b, stresses between the first layer 810a and the second layer 820a can be reduced.

Figure 9:
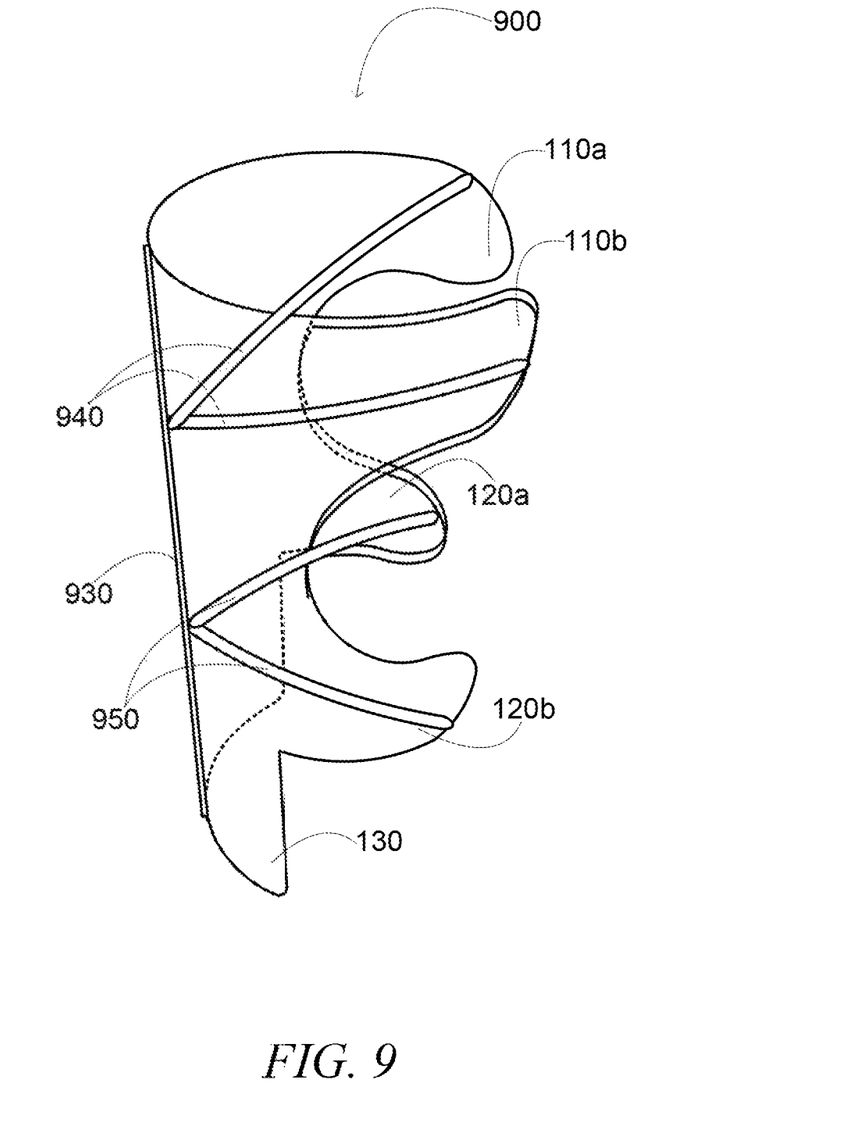
FIG. 9 is a schematic illustrating a spring mechanism used to achieve a clasping effect of a protective dental device according to one embodiment.

FIG. 9 is a schematic illustrating a spring mechanism used to achieve a clasping effect of a protective dental device 900. For example, a ridge 930 of the spring mechanism can be positioned along a spine of the protective dental device 900. A first spring extension 940 extends from the ridge of the spring mechanism through the first pair of opposing flanges 110a and 110b, and a second spring extension 950 extends from the ridge of the spring mechanism through the second pair of opposing flanges 120a and 120b of the protective dental device 900. This provides a clasping effect around a drill head of a dental drill.

Embodiments described herein provide protection and comfort for a patient during a dental procedure. Each of the protective dental devices described herein provides complete protection of a patient's mucosa and tongue from the different angles of approach by a dental drill. Each of the protective dental devices can be easily rotated by a dental practitioner without the use of tools.

Embodiments described herein include the following aspects.

(1) A dental device includes a rounded flexible device configured to attach onto a head of a dental drill. The rounded flexible device has a first pair of opposing horizontal protrusions positioned at a first end of the rounded flexible device; a second pair of opposing horizontal protrusions positioned at a mid-portion of the rounded flexible device, wherein the first pair of opposing horizontal protrusions extend horizontally beyond the second pair of opposing horizontal protrusions; and a central vertical protrusion positioned at a second end of the rounded flexible device. The first pair and the second pair of opposing horizontal protrusions are configured to partially encircle the head of the dental drill, and the central vertical protrusion is configured to extend a length of a rotating drill bit of the dental drill.

(2) The dental device of (1), wherein the rounded flexible device is configured to rotate about the head of the dental drill.

(3) The dental device of either one of (1) or (2), wherein the central vertical protrusion is configured to extend beyond a length of the rotating dental bit of the dental drill.

(4) The dental device of any one of (1) through (3), wherein the rounded flexible device comprises a biocompatible plastic material.

(5) The dental device of any one of (1) through (4), wherein the biocompatible plastic material includes one or more of polylactic acid (PLA), poly(lactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), silicone, polyurethane, thermoplastic elastomer (TPE) such as a styrenic block copolymer (TPE-s), a thermoplastic olefin (TPE-o), an elastomeric alloy (TPE-v or TPV), a thermoplastic polyurethane (TPU), a thermoplastic copolyester (TPE-E), or a thermoplastic polyamide.

(6) The dental device of any one of (1) through (5), wherein the rounded flexible device comprises a laminated material.

(7) The dental device of any one of (1) through (6), wherein the laminated material comprises a first layer having a first coefficient of thermal expansion (CTE) and a second layer having a second CTE.

(8) The dental device of any one of (1) through (7), wherein the first CTE differs from the second CTE.

(9) The dental device of any one of (1) through (8), wherein the laminated material comprises a first layer having a first filler and a second layer having a second filler.

(10) The dental device of any one of (1) through (9), wherein a first coefficient of thermal expansion (CTE) of the first filler differs from a second CTE of the second filler.

(11) The dental device of any one of (1) through (10), wherein the rounded flexible device comprises one or more horizontal ridges across an outside surface of the rounded flexible device.

(12) The dental device of any one of (1) through (1), wherein the rounded flexible device comprises one or more horizontal depressions across an outside surface of the rounded flexible device.

(13) The dental device of any one of (1) through (12), wherein the rounded flexible device comprises a spring mechanism configured to clasp the head of the dental drill.

(14) A dental device includes a dental drill and a rounded flexible device attached to a head of the dental drill. The rounded flexible device has a first pair of opposing horizontal protrusions positioned at a first end of the rounded flexible device; a second pair of opposing horizontal protrusions positioned at a mid-portion of the rounded flexible device, wherein the first pair of opposing horizontal protrusions extend horizontally beyond the second pair of opposing horizontal protrusions; and a central vertical protrusion positioned at a second end of the rounded flexible device. The first pair and the second pair of opposing horizontal protrusions are configured to partially encircle the head of the dental drill, and the central vertical protrusion is configured to extend a length of a rotating drill bit of the dental drill.

(15) The dental device of (14), wherein the rounded flexible device is autoclaved to the dental drill.

(16) The dental device of either one of (14) or (15), wherein the rounded flexible device comprises a biocompatible plastic material.

(17) The dental device of any one of (14) through (16), wherein the rounded flexible device comprises a laminated material.

(18) The dental device of any one of (14) through (17), wherein the rounded flexible device comprises one or more horizontal ridges across an outside surface of the rounded flexible device.

(19) The dental device of any one of (14) through (18), wherein the rounded flexible device comprises one or more horizontal depressions across an outside surface of the rounded flexible device.

(20) The dental device of any one of (14) through (19), wherein the rounded flexible device comprises a spring mechanism configured to clasp the head of the dental drill.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components.

The foregoing discussion describes merely exemplary embodiments of the present disclosure. As will be understood by those skilled in the art, the present disclosure may be embodied in other specific forms without departing from the spirit or essential characteristics thereof. Accordingly, the disclosure is intended to be illustrative, but not limiting of the scope of the disclosure, as well as the claims. The disclosure, including any readily discernible variants of the teachings herein, defines in part, the scope of the foregoing claim terminology such that no inventive subject matter is dedicated to the public.

The invention claimed is:

1. A dental device, comprising:
 a rounded flexible device configured to removably attach onto a head of a contra-angled dental drill, wherein the rounded flexible device includes:
  a first pair of opposing and spaced-apart rounded top protrusions positioned at a first end of the rounded flexible device, wherein, in a side elevational view of the rounded flexible device, the first pair of rounded top protrusions extend in a first direction,
  a central protrusion positioned at a second end of the rounded flexible device opposite the first end of the rounded flexible device,
  a second pair of opposing and spaced-apart rounded bottom protrusions positioned at a portion of the rounded flexible device between the first pair of rounded top protrusions and the central protrusion, wherein, in the side elevational view of the rounded flexible device, the second pair of rounded bottom protrusions extend in the first direction less than an amount by which the first pair of rounded top protrusions extend in the first direction, and
  a central linear body portion that extends linearly from the first end of the rounded flexible device to the second end of the rounded flexible device;
 a ridge at the central linear body portion, the ridge extending from the first end of the rounded flexible device to the second end of the rounded flexible device;
 a first pair of opposing spring extensions that extend from the ridge to respective ends of the first pair of rounded top protrusions and configured to bias the first pair of rounded top protrusions toward each other; and
 a second pair of opposing spring extensions that extend from the ridge to respective ends of the second pair of rounded bottom protrusions and configured to bias the second pair of rounded bottom protrusions toward each other,
 wherein a first set of one of the rounded top and one of the rounded bottom protrusions define a first receptacle therebetween, and a second set of another of the rounded top and another of the rounded bottom protrusions define a second receptacle therebetween,
 wherein the first pair and the second pair of rounded top and bottom protrusions are configured to partially encircle the head of the contra-angled dental drill such that a drill handle of the contra-angled dental drill is provided in one of the first and second receptacles and extends between corresponding rounded top and bottom protrusions of the first or second sets,
 wherein the central protrusion is sized to extend linearly a length of a rotating drill bit of the contra-angled dental drill when the first pair and the second pair of rounded protrusions partially encircle the head of the contra-angled dental drill, and
 wherein a length of the central protrusion is defined from the second end of the rounded flexible device to the rounded bottom protrusions of the second pair, said length of the central protrusion being less than a length of the rounded flexible device from the rounded bottom protrusions of the second pair to the first end of the rounded flexible device.

2. The dental device of claim 1, wherein the rounded flexible device is configured to rotate about the head of the contra-angled dental drill.

3. The dental device of claim 1, wherein the central protrusion is configured to extend beyond a length of the rotating dental bit of the contra-angled dental drill.

4. The dental device of claim 1, wherein the rounded flexible device comprises a biocompatible plastic material.

5. The dental device of claim 4, wherein the biocompatible plastic material includes one or more of polylactic acid (PLA), poly(lactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), silicone, polyurethane, thermoplastic elastomer (TPE) such as a styrenic block copolymer (TPE-s), a thermoplastic olefin (TPE-o), an elastomeric alloy (TPE-v or TPV), a thermoplastic polyurethane (TPU), a thermoplastic copolyester (TPE-E), or a thermoplastic polyamide.

6. A dental device, comprising:
 a contra-angled dental drill; and
 a rounded flexible device removably attached to a head of the contra-angled dental drill, wherein the rounded flexible device includes:
  a first pair of opposing and spaced-apart rounded top protrusions positioned at a first end of the rounded flexible device, wherein, in a side elevational view of the rounded flexible device, the first pair of rounded top protrusions extend in a first direction,
  a central protrusion positioned at a second end of the rounded flexible device opposite the first end of the rounded flexible device,
  a second pair of opposing and spaced-apart rounded bottom protrusions positioned at a portion of the rounded flexible device between the first pair of rounded top protrusions and the central protrusion, wherein, in the side elevational view of the rounded flexible device, the second pair of rounded bottom protrusions extend in the first direction less than an amount by which the first pair of rounded top protrusions extend in the first direction, and a central linear body portion that extends linearly from the first end of the rounded flexible device to the second end of the rounded flexible device, wherein a first set of one of the rounded top and one of the rounded bottom protrusions define a first receptacle therebetween, and a second set of another of the rounded top and another of the rounded bottom protrusions define a second receptacle therebetween, wherein the first pair and the second pair of rounded top and bottom protrusions are configured to partially encircle the head of the contra-angled dental drill such that a drill handle of the contra-angled dental drill is provided in one of the first and second receptacles and extends between corresponding rounded top and bottom protrusions of the first or second sets, wherein the central protrusion is sized to extend linearly a length of a rotating drill bit of the contra-angled dental drill when the first pair and the second pair of rounded protrusions partially encircle the head of the contra-angled dental drill, and wherein a length of the central protrusion is defined from the second end of the rounded flexible device to the rounded bottom protrusions of the second pair, said length of the central protrusion being less than a length of the rounded flexible device from the rounded bottom protrusions of the second pair to the first end of the rounded flexible device.

7. The dental device of claim 6, wherein the rounded flexible device is autoclavable.

8. The dental device of claim 6, wherein the rounded flexible device comprises a biocompatible plastic material.

9. The dental device of claim 6, wherein the rounded flexible device comprises a laminated material.

10. The dental device of claim 6, wherein the rounded flexible device comprises one or more horizontal ridges across an outside surface of the rounded flexible device.

11. The dental device of claim 6, wherein the rounded flexible device comprises one or more horizontal depressions across an outside surface of the rounded flexible device.

12. The dental device of claim 6, further comprising:

a ridge at the central linear body portion, the ridge extending from the first end of the rounded flexible device to the second end of the rounded flexible device;

a first pair of opposing spring extensions that extend from the ridge to respective ends of the first pair of rounded top protrusions and configured to bias the first pair of rounded top protrusions toward each other; and a second pair of opposing spring extensions that extend from the ridge to respective ends of the second pair of rounded bottom protrusions and configured to bias the second pair of rounded bottom protrusions toward each other.

* * * * *